United States Patent
Pohl et al.

(10) Patent No.: US 6,489,513 B2
(45) Date of Patent: Dec. 3, 2002

(54) PROCESS FOR THE PREPARATION OF ENANTIOMERICALLY PURE (5, 5'-DICHLORO-6,6'-DIMETHOXY-BIPHENYL-2,2'-DIYL)- BIS(DIPHENYLPHOSPHINE OXIDES)

(75) Inventors: Torsten Pohl, Köln (DE); Thomas Prinz, Leverkusen (DE); Guido Giffels, Bonn (DE); Wolfram Sirges, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/010,176

(22) Filed: Nov. 13, 2001

(65) Prior Publication Data

US 2002/0058814 A1 May 16, 2002

(30) Foreign Application Priority Data

Nov. 14, 2000 (DE) ......................... 100 56 310

(51) Int. Cl.$^7$ .................................. C07F 9/53
(52) U.S. Cl. .......................... 568/14; 568/17
(58) Field of Search ............... 568/13, 14, 17

(56) References Cited

U.S. PATENT DOCUMENTS

| | | | |
|---|---|---|---|
| 4,556,740 A | 12/1985 | Hansen et al. | 568/13 |
| 5,302,738 A | 4/1994 | Foricher et al. | 558/162 |
| 5,457,219 A * | 10/1995 | Foricher et al. | 556/404 |
| 5,510,503 A | 4/1996 | Laue et al. | 556/21 |
| 5,600,015 A * | 2/1997 | Broger et al. | 568/396 |
| 5,621,128 A * | 4/1997 | Jendralla | 556/136 |
| 5,710,339 A | 1/1998 | Laue et al. | 568/16 |
| 5,801,216 A | 9/1998 | Laue et al. | 556/16 |
| 6,075,154 A * | 6/2000 | Gonda et al. | 549/328 |
| 6,162,929 A * | 12/2000 | Foricher et al. | 549/216 |

OTHER PUBLICATIONS

Schmid, Rudolf et al: "Axially dissymmetric diphosphines in the biphenyl series: synthesis of (6,6'–dimethoxybiphenyl–2,2'–diyl)bis(diphenylphosphine) ('MeO–Biphep") and analogs via an ortho–lithiation/iodination Ullmann–reaction approach" Helv. Chim. Acta (1991), 74(2), 370–89, XP002097708 ★Seite 372★.

* cited by examiner

*Primary Examiner*—Jean F. Vollano
(74) *Attorney, Agent, or Firm*—Joseph C. Gil; Richard E. L. Henderson; Godfried R. Akorli

(57) ABSTRACT

The invention relates to the preparation of enantiomerically pure bis-diphenylphosphine oxides in a particularly advantageous manner by (1) reacting an aromatic bromine compound with a diphenylphosphinic chloride in a mixture of tetrahydrofuran and an aromatic hydrocarbon to give a diphenylphosphine oxide, which is isolated from a solution in an aromatic hydrocarbon by adding a saturated aliphatic hydrocarbon; (2) metalating the resulting diphenylphosphine oxide in the 6-position and reacting the metalated diphenylphosphine oxide with iodine at temperatures not less than −25° C. in such a way that a small amount of iodine is always present in excess, giving a 2-iodo-diphenylphosphine oxide; (3) preparing a racemic bis-diphenylphosphine oxide from the resulting 2-iodo-diphenylphosphine oxide using copper and an aromatic hydrocarbon solvent and crystallizing the racemic bis-diphenylphosphine oxide from a solution in an aromatic hydrocarbon; and (4) separating isomers using an enantiomerically pure mono- or dicarboxylic acid to obtain a first enantiomer by crystallization from a solution in an aromatic hydrocarbon and obtaining a second enantiomer by hydrolysis and subsequent crystallization from a solution in an aromatic hydrocarbon.

9 Claims, No Drawings

PROCESS FOR THE PREPARATION OF ENANTIOMERICALLY PURE (5, 5'-DICHLORO-6,6'-DIMETHOXY-BIPHENYL-2,2'-DIYL)- BIS(DIPHENYLPHOSPHINE OXIDES)

BACKGROUND OF THE INVENTION

The present invention relates to an improved process for the preparation of enantiomerically pure (5,5'-dichloro-6,6'-dimethoxybiphenyl-2,2'-diyl)-bis(diphenylphosphine-oxides) starting from 5-bromo-2-chloro-anisole and phosphorus oxychlorides of the type O=P(phenyl)$_2$(Cl).

Such bis-diphenylphosphine oxides can be reduced to give the corresponding bis-diphenylphosphines, which are used as ligands for metal complexes. Such metal complexes are for their part of importance as catalysts for enantioselective hydrogenations (see DE-A1 195 22 293 and the corresponding U.S. Pat. No. 5,710,339 and 5,801,261).

Likewise known from this literature is a multi-stage process for the preparation of enantiomerically pure (5,5'-dichloro-6,6'-dimethoxybiphenyl-2,2'-diyl)-bis(diphenylphosphine oxides). In this process, in a first stage, 5-bromo-2-chloroanisole is reacted by a selective monometalation with a phosphorus oxychloride of the type O=P(phenyl)$_2$(Cl), giving a (4-chloro-3-methoxyphenyl)diphenylphosphine oxide. The metalation is carried out with magnesium in tetrahydrofuran, the phosphorus oxychloride is used as a solution in tetrahydrofuran, and the product is isolated by concentrating a solution in methylene chloride by evaporation and stirring with tert-butyl methyl ether. The product is produced in a yield of 70%.

In a second stage, the (4-chloro-3-methoxyphenyl)diphenyl-phosphine oxide is converted into the corresponding 2-iodo compound.

For this purpose, lithium diisopropylamide, dissolved in tetrahydrofuran, is added to a solution of the starting phosphine oxide in tetrahydrofuran at −70° C., the mixture is heated to 0° C., cooled to −76° C., and then, at this temperature, a solution of iodine in tetrahydrofuran is added dropwise. Work-up is carried out by treating with aqueous sodium sulfite solution, then extracting with ethyl acetate and stripping off the extractant. This gives the product in a yield of 80%.

In a third stage, the (4-chloro-2-iodo-3-methoxyphenyl)diphenyl-phosphine oxide is reacted with copper powder in dimethylformamide over the course of 16 hours to give racemic (5,5'-dichloro-6,6'-dimethoxybiphenyl-2,2'-diyl)-bis(diphenylphosphine oxide). The latter compound is isolated by filtration, removal of the dimethylformamide from the filtrate, and stirring with tert-butyl methyl ether.

Finally, in a fourth stage, the racemic (5,5'-dichloro-6,6'-dimethoxy-biphenyl-2,2-diyl)-bis(diphenylphosphine oxide) is separated into its enantiomers using enantiomerically pure mono- or dicarboxylic acids. Here, both forms of enantiomerically pure mono- or dicarboxylic acid have to be used one after the other and complex extractions and filtrations have to be carried out.

The known overall process for the preparation of the bis-diphenyl-phosphine oxides is disadvantageous, not very suitable, and uneconomic for use on a relatively large scale, since it produces products in unsatisfactory yields, in many cases requires partly toxic solvents, is very complicated in terms of process engineering, requires the use of very low temperatures (down to −76° C.) and long reaction times, and requires the use of large amounts of solvents and auxiliaries.

There is therefore still the need for a process for the preparation of such bis-diphenylphosphine oxides, with which the latter are accessible in a more simple, more efficient and more cost-effective manner, and with which a preparation on a relatively large scale can also be carried out without problems.

SUMMARY OF THE INVENTION

We have now found a process for the preparation of enantiomerically pure bis-diphenylphosphine oxides of the formula (I)

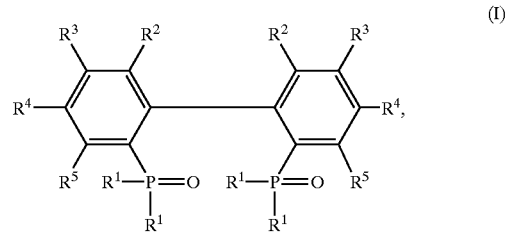

in which $R^1$ is phenyl, naphthyl, heteroaryl having 4 or 5 carbon atoms and 1 or 2 heteroatoms selected from the group consisting of nitrogen, oxygen, and sulfur, or cyclohexyl, wherein each $R^1$ is optionally substituted by R', OR', NO$_2$, NH$_2$, NHR', or NR'$_2$ in which each R'is C$_1$–C$_6$-alkyl, $R^2$ is C$_1$–C$_4$-alkoxy, $R^3$ is hydrogen, fluorine, chlorine, or bromine, and $R^4$ and $R^5$, independently of one another, are hydrogen, fluorine, chlorine, bromine, C$_1$–C$_6$-alkyl, or C$_1$–C$_6$-alkoxy, comprising (1) in a first stage, selectively monometalating a bromine compound of the formula

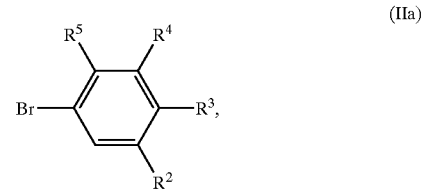

in which $R^2$ to $R^5$ have the meanings given for formula (I), in a solvent comprising a mixture of tetrahydrofuran and an aromatic hydrocarbon and reacting the resultant metalated compound with a diphenylphosphinic chloride of the formula (II)

in which $R^1$ has the meaning given for formula (I), which is added without solvent to the metalated compound, to give a diphenylphosphine oxide of the formula (III)

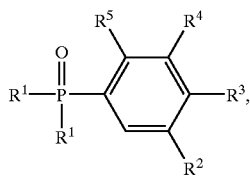

in which $R^1$ to $R^5$ have the meanings given in formula (I), which is isolated from a solution in an aromatic hydrocarbon by adding a saturated aliphatic hydrocarbon, (2) in a second stage, metalating the diphenylphosphine oxide of the formula (III) in the 6-position and reacting the resultant metalated compound with iodine at a temperature of not less than −25° C., wherein the metalated diphenylphosphine oxide of the formula (III) and iodine are metered in simultaneously such that a small amount of iodine is always present in excess, to give a 2-iodo-diphenyl-phosphine oxide of the formula (IV)

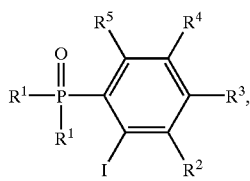

in which $R^1$ to $R^5$ have the meanings given for formula (I), which is separated off in dissolved form in an aromatic hydrocarbon, (3) in a third stage, converting the 2-iodo-diphenylphosphine oxide of the formula (IV) with copper (preferably dendritic copper) in an aromatic hydrocarbon solvent into a racemic bis-diphenylphosphine oxide of the formula (I), which is crystallized from absolution in an aromatic hydrocarbon, and (4) in a fourth stage, separating the racemic bis-diphenylphosphine oxide of the formula (I) into its enantiomers by crystallization with an enantiomerically pure mono- or dicarboxylic acid, wherein a first enantiomer is obtained by crystallization from a solution in an aromatic hydrocarbon and a second enantiomer is obtained by hydrolysis and subsequent crystallization from a solution in an aromatic hydrocarbon.

DETAILED DESCRIPTION OF THE INVENTION

In the formulas (I) to (IV), $R^1$ is preferably unsubstituted phenyl, unsubstituted naphthyl, heteroaryl having 4 or 5 carbon atoms and 1 or 2 heteroatoms selected from the group consisting of oxygen and sulfur, or unsubstituted cyclohexyl.

In the formulas (I), (IIa), (III) and (IV)

$R^2$ is preferably methoxy, $R^3$ is preferably fluorine, chlorine, or bromine (particularly chlorine), and $R^4$ and $R^5$ are preferably hydrogen.

The aromatic hydrocarbons are, for example, benzene, toluene, or xylenes. Preference is given to toluene.

The saturated aliphatic hydrocarbons may, for example, be those having boiling points of more than 30° C. (at atmospheric pressure). Preference is given to straight-chain or branched pentanes, hexanes, heptanes, and octanes. Particular preference is given to n-pentane.

In the first stage, the metalation can be carried out, for example, using magnesium, which can be activated, where necessary, for example, by adding a small amount of iodine. For the metalation, it is possible to use, for example, 1 to 1.5 mol of magnesium, based on 1 mol of bromine compound of the formula (IIa). The solvent mixture to be used for the metalation can comprise, for example, 20 to virtually 100% by volume of tetrahydrofuran and brought to 100% by volume using aromatic hydro-carbon. The solvent mixture preferably comprises 40 to 60% by volume (particularly 45 to 55% by volume) of tetrahydrofuran and brought to 100% by volume using aromatic hydrocarbon.

The procedure can be carried out, for example, by additionally introducing magnesium, a small amount of iodine, and the solvent mixture, heating the mixture to a temperature in the range from 30 to 80° C., then metering in a bromine compound of the formula (IIa) dissolved in the same solvent mixture at a temperature in the range from 30 to 80° C. and, where appropriate, when the metered addition is complete, refluxing further, e.g., for 5 to 60 minutes. The phosphinic chloride of the formula (II) is then added not in dissolved form but without a diluent, for example, with cooling to temperatures in the range from −10 to +15° C. Finally, the mixture can be further after-stirred, for example, for 30 to 250 minutes, at temperatures in the range from 0 to 30° C.

The reaction mixture present after the first stage has been carried out can be worked up, for example, by pouring it onto iced water, separating off the organic phase, extracting the aqueous phase with an aromatic hydrocarbon, combining the organic phase and the extract, washing with dilute aqueous alkaline solution and water, and concentrating by evaporation. Advantageously, the aim is a solution of the prepared diphenylphosphine oxide of the formula (III) in and aromatic hydrocarbon that is as concentrated as possible but from which no solid constituents precipitate. According to the invention, a saturated aliphatic hydrocarbon is then added and after, for example, 5 to 20 hours, the formed, readily filterable precipitate is filtered off, optionally after-washed with the saturated aliphatic hydrocarbon, and dried.

In this way, it is possible to obtain a diphenylphosphine oxide of the formula (III) in the form of a white powder in yields of more than 80% and in purities of more than 92%. By dispensing with the addition of the phosphinic chloride of the formula (II) in a solvent, it is possible to work overall with less solvent, thus saving on solvent and achieving a higher space-time yield.

In the second stage, the metalating agent used may be, for example, butyllithium or lithium diisopropylamide. The latter is preferred.

The procedure may involve, for example, initially introducing the diphenylphosphine oxide of the formula (III) in a solvent, e.g., tetrahydro-furan, cooling it to, for example, −25 to 0° C., and, at this temperature, metering in the metalating agent, e.g., dissolved in tetrahydrofuran containing hydrocarbons, such that the temperature can be maintained in the range from −25 to 0° C. by cooling. This gives a solution (A). Separately, a solution of iodine in, for example, tetrahydrofuran can be prepared and also cooled to, for example, −25 to 0° C. This gives a solution (B). Then, a reaction vessel is charged with a small amount of solvent, e.g., tetrahydro-furan, and at, for example, −25 to 0° C., and then, at, for example, −25 to 0° C., solution (A) and solution (B) are metered in simultaneously such that a small amount of iodine is always present in excess. This can be readily checked from the color of the reaction mixture. Dark colors indicate an iodine excess. The temperature is preferably maintained at −25° C. to −1 0° C. during the reaction. To complete the reaction, following the metered addition of solutions (A) and (B), it is possible, where appropriate, to after-stir for a further, for example, 10 to 150 minutes at, for example, −10 to +10° C. Thereafter, excess iodine that is still present is expediently removed, e.g., by adding a dilute aqueous solution of sodium thiosulfate.

The reaction mixture present after the second stage has been carried out can be worked up, for example, by first separating off the organic phase, extracting the remaining aqueous phase with an extractant, e.g., an aromatic hydrocarbon, where necessary, washing the organic phase combined with the extract with water, and concentrating by evaporation. In this way, it is possible to obtain 2-iodo-diphenylphosphine oxides of the formula (IV) in yields of more than 90% and in the form of, for example, 15 to 30% strength by weight solutions in an aromatic hydro-carbon. Such solutions can be used directly in the third process stage.

The second process stage carried out according to the invention is characterized by the use of temperatures that can be maintained with little technical expenditure, shortened metered addition times, yield increases, and a simple work-up option.

In the third stage, a dendritic copper is preferably used, as described in Glossary of Terms Relating to Particle Technology, Edition 1 st May 1996. Such copper can have an average particle size of, for example, 1 to 100 μm (preferably 30 to 50 μm), a surface area of, for example, 0.04 to 1 m²/g (preferably 0.07 to 0.5 m²/g), and a purity of more than 99.5% (preferably more than 99.7%). Dendritic copper to be used according to the invention is available commercially.

The procedure may involve, for example, initially introducing dendritic copper together with the aromatic hydrocarbon and, at a temperature of, for example, 70 to 140° C., metering in the solution of a 2-iodo-diphenylphosphine oxide of the formula (IV) obtained in the second stage. It is possible to use, for example, 1 to 10 mol (preferably 2 to 8 mol) of dendritic copper per mole of 2-iodo-diphenylphosphine oxide of the formula (IV). When the metered addition is complete, it is possible, where necessary, to after-stir for a further 1 to 5 hours at 70 to 140° C. The metered addition and after-stirring time can together be, for example, 3 to 8 hours. For work-up, it is possible, for example, to filter the hot reaction mixture, to wash the filter cake with a solvent, e.g., a chlorinated hydro-carbon, to evaporate the washing solution to dryness, to add the solid obtained to the filtrate, and to heat this mixture to reflux temperature. It is also possible to after-wash the filter cake with an aromatic hydrocarbon heated, for example, to 70 to 140° C., to add this wash solution to the first filtrate, and to heat the mixture to reflux temperature. Where appropriate, it is possible to remove some of the aromatic hydrocarbon, e.g., by distillation. Upon cooling to, for example, 0 to 25° C., the prepared racemic bis-diphenylphosphine oxide of the formula (I) then precipitates out and can be collected, for example, by filtration and subsequent drying, where necessary, in a vacuum and at elevated temperature.

The third reaction stage carried out according to the invention is characterized by the use of cost-effective and low-toxicity solvents, by simple work-up, and shorter reaction times.

In the fourth stage, it is possible, for example, to react, at elevated temperature, the racemic bis-diphenylphosphine oxide of the formula (I) dissolved, for example, in a chlorinated hydrocarbon, with a solution of a pure enantiomer of dibenzoyltartaric acid, for example, in an ester, and to cool the reaction mixture slowly, for example, over the course of from 2 to 6 hours, to 10 to 25° C. In the process, a salt precipitates out that can be separated off, for example by filtration.

The salt can be further processed, for example, by taking it up in an aromatic hydrocarbon, washing it with dilute aqueous acid and dilute aqueous base, then heating the organic phase to boiling and evaporating off or adding just enough aromatic hydrocarbon such that a virtually saturated solution is present at elevated temperature. After cooling, for example, to 10 to 30° C., the one enantiomerically pure form of the bis-diphenylphosphine oxide of the formula (I) that crystallizes out can be separated off. This generally gives the product with an enantiomer excess ee of more than 99%.

The filtrate from the work-up following the reaction with a pure enantiomer of dibenzoyltartaric acid can be worked up initially in a manner similar to the salt taken up with an aromatic hydrocarbon, for example, by washing it directly with dilute acid and then with dilute aqueous base. By changing the solvent, e.g., to an aromatic hydrocarbon, concentrating by evaporation, and cooling, it is possible to obtain a solid that is a racemic feed material. From the filtrate from the separation of the racemic feed material, it is possible, by further concentration by evaporation and cooling, to obtain the second enantiomer of the bis-phenylphosphine oxide of the formula (I) generally with an enantiomer excess ee of more than 99%.

The fourth process stage according to the invention is characterized by a saving of approximately 50% of enantiomerically pure mono- or dicarboxylic acid and a simple work-up.

If enantiomerically pure bis-diphenylphosphine oxide of the formula (I) prepared according to the invention is to be reduced to the corresponding bis-diphenylphosphine, this can be achieved in a known manner, for example, using trichlorosilane as reducing agent in accordance with the literature given in the introduction above.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Preparation of (4-Chloro-3-methoxyphenyl) diphenylphosphine oxide

Under argon, 1 mol of Mg turnings and a spatula tip of iodine in a mixture of 100 ml of tetrahydrofuran and 100 ml of toluene were heated to 60° C. Over the course of 10 minutes, 200 g of 5-bromo-2-chloroanisole in a mixture of 200 ml of tetrahydrofuran and 200 ml of toluene were added dropwise. During the dropwise addition, the internal temperature was maintained at 60° C. by cooling. When the dropwise addition was complete, the reaction mixture was heated to reflux temperature and after-stirred for 30 minutes at this temperature. The mixture was then cooled to 0° C.

and 236.8 g of diphenylphosphinic chloride were added dropwise over the course of 45 minutes. The internal temperature was maintained during this operation between 0 and 5° C. The reaction mixture was after-stirred for 5 minutes at 0° C., the cooling was switched off, and the mixture was stirred for a further 2 hours. For work-up, the reaction mixture was poured onto 1.6 liter of iced water, the organic phase was separated off, and the aqueous phase was washed again with 2×400 ml of toluene. The combined organic phases were washed with 400 ml of 2.5% strength by weight aqueous soda solution and then with 400 ml of water, and then concentrated on a rotary evaporator to a volume of 200 ml. Then, with stirring, 300 ml of n-pentane were added dropwise. The solid that precipitated out overnight was filtered off with suction, washed with n-pentane, and dried. This gave 203.5 g of a white solid. The yield was 82% and the purity was 94%.

Example 2

Preparation of (4-chloro-2-iodo-3-methoxyphenyl) diphenylphosphine oxide

The reaction was carried out under a protective-gas atmosphere, and peroxide-free tetrahydrofuran was used.

51.4 g of (4-chloro-3-methoxyphenyl)diphenylphosphine oxide were dissolved in 300 ml of tetrahydrofuran in a reaction vessel and cooled to −20° C. 90 ml of lithium diisopropylamide in the form of a 2 molar solution in a mixture of tetrahydrofuran, ethylbenzene, and hexane were added dropwise to this solution. The dropwise addition was regulated such that the internal temperature could be maintained at −15° C.

In another reaction vessel, 150 ml of tetrahydrofuran were introduced and cooled to −20° C. The contents of the first reaction vessel and a solution of 43.9 g of iodine in 150 ml of tetrahydrofuran were simultaneously added dropwise thereto such that the internal temperature could be maintained at −1 5° C. By making a visual check, it was ensured that a slight iodine excess was always present in the reaction mixture.

After the two solutions had been added dropwise in their entirety, the reaction vessel was brought to an internal temperature of 0° C., and the mixture was after-stirred for 1 hour at this temperature. The reaction mixture was then added to a solution of 60 g of sodium thiosulfate in 500 ml of water, which was likewise cooled to 0° C., and 250 ml of water were additionally added.

The organic phase was separated off and the aqueous phase was extracted with 2×125 ml of toluene. The combined organic phases were washed with 125 ml of water and concentrated on a rotary evaporator to a volume of 250 ml. The resulting solution had a content of 24% by weight of (4-chloro-2-iodo-3-methoxyphenyl)diphenylphosphine oxide, which corresponds to a yield of 93.5%.

Example 3

Preparation of Racemic (5,5'-Dichloro-6,6'-dimethoxybiphenyl-2,2'-diyl)-bis-(diphenylphosphine oxide)

31.7 g of dendritic copper powder with an average particle size of 36 $\mu$m and a surface area of 0.13 m$^2$ were introduced into 500 ml of toluene and heated to reflux temperature. Over the course of one hour, a solution of 0.128 mol of (4-chloro-2-iodo-3-methoxyphenyl)diphenyl-phosphine oxide in 250 ml of toluene was added dropwise. The reaction mixture was refluxed for 3 hours and then filtered at 100° C.

over Celite® filter aid, and the filtrate was set aside. The filter cake was washed with 3×100 ml of dichloromethane, the washing solution was evaporated to dryness on a rotary evaporator, and the solid that was left behind was added to the filtrate of the mixture. The resulting suspension was then heated to reflux, during which all of the solid present was again dissolved. The mixture was then cooled slowly to room temperature with stirring. The solid then present was filtered off with suction and washed with 2×50 ml of cold toluene. The solid was then dried at 50° C. in a vacuum. 35.7 g of a white solid with a content of 83% by weight of the product were isolated. This corresponds to a yield of 68%.

Example 4

Resolution of racemic (5,5'-dichloro-6,6'-dimethoxybiphenyl-2,2'-diyl)-bis-(dimethylphosphine oxide) into its enantiomers 0.06 mol of the product from Example 3 were dissolved in 360 ml of methylene chloride and heated to reflux temperature. A solution of 10.8 g of anhydrous (+)-dibenzoyltartaric acid in 195 ml of ethyl acetate was then added dropwise, the mixture being maintained at reflux temperature. After everything had been added, the mixture was left to cool to room temperature with slow stirring and after-stirred for a further 1 hour (4 hours in total). The salt that precipitated out was filtered off and washed with 2×30 ml of a 2:1 mixture of methylene chloride/ethyl acetate.

The salt was worked up by first taking it up in 100 ml of toluene and extracting it with 2×200 ml of 1 N aqueous sodium hydroxide solution. By briefly warming, the solid present in the organic phase was brought into solution. The organic phase was then washed with in each case 200 ml of 1 N aqueous hydrochloric acid, 1 N aqueous sodium hydroxide solution and water. 64.5 g of toluene were then distilled off on a rotary evaporator. The resulting suspension was heated to reflux and sufficient toluene was added as was necessary to dissolve all solid that was present. The solution was then cooled to room temperature and the product that crystallized out was filtered off and dried. This gave (+)-(5, 5'-dichloro-6,6'-dimethylbiphenyl-2,2'-diyl)-bis (diphenylphosphine oxide) in a yield of 32% and in an enantiomer purity of 99.2%.

The filtrate that was obtained following removal of the salt from the reaction with (+)-dibenzoyltartaric acid was washed with 2×200 ml of 1 N aqueous sodium hydroxide solution. The organic phase was then washed with in each case 200ml of 1 N aqueous hydrochloric acid, 1 N aqueous sodium hydroxide solution, and water. The mixture was concentrated by evaporation to an amount of 250 g, then 180 g of toluene were added and the mixture was again concentrated by evaporation to an amount of 125 g. The solution then present was cooled to room temperature and the solid that precipitated out was filtered. It was dried and 28% by weight of the racemic feed material were recovered.

60 g of toluene were distilled off from the filtrate from the removal of the racemic feed material on a rotary evaporator. This gave a suspension, which was heated to reflux and sufficient toluene was added as was necessary for all of the solid to just dissolve again. The solution was again cooled to room temperature and the product that crystallized out during this operation was filtered off and dried. In this way, (−)-5,5'-dichloro-6,6'-dimethoxybiphenyl-2,2'-diyl)-bis (diphenylphosphine oxide) was isolated in a yield of 26% in an enantiomer purity of 99.8%.

The overall recovery of the racemic starting material used was thus 86%.

Example 5

(not according to the invention) Reduction of the (+)-(5,5'-dichloro-6,6'-dimethoxybiphenyl-2,2'-diyl)-bis-(diphenylphosphine oxide) obtained in Example 4 to give the corresponding phosphine 32 ml of tributylamine were added to a solution of 13.5 mmol of (+)-(5,5'-dichloro-6,6'-dimethoxybiphenyl-2,2'-diyl)-bis(diphenylphosphine oxide) in 100 ml of xylene (purified isomer mixture), the mixture was heated to 110° C. under an argon atmosphere and, at this temperature, a solution of 13.6 g of trichlorosilane in 50 ml of xylene (purified isomer mixture) was added dropwise over the course of half an hour. The mixture was refluxed for 3 hours. The solution was then cooled to room temperature, 290 ml of methylene chloride were added, then the mixture was cooled to 0° C., and, at this temperature, sufficient 10% strength by weight aqueous sodium hydroxide solution was added to achieve a pH of 10. The resulting suspension was filtered under a protective-gas frit that had been filled with 5 g of aluminum oxide. The organic phase was transferred to a second flask and the aqueous phase was extracted with 290 ml of methylene chloride. The combined methylene chloride phases were washed twice with 250 ml of water under argon. The organic phase was then concentrated by evaporation in a vacuum to a volume of 100 ml. Even upon concentration, the product started to crystallize. The suspension was stored overnight at 5° C., then filtered with suction, and the solid product was dried in a vacuum. 7.4 g of a pale yellow solid with a content of 95.5% of (+)-(5,5'-dichloro-6,6'-dimethoxybiphenyl-2,2'-diyl)-bis(diphenylphosphine) were obtained. This corresponds to a yield of 89%.

What is claimed is:

1. A process for the preparation of enantiomerically pure bis-diphenylphosphine oxides of the formula (I)

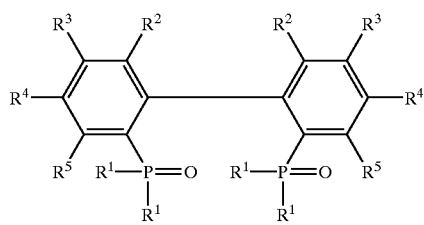

in which $R^1$ is phenyl, naphthyl, heteroaryl having 4 or 5 carbon atoms and 1 or 2 heteroatoms selected from the group consisting of nitrogen, oxygen, and sulfur, or cyclohexyl, wherein each $R^1$ is optionally substituted by R', OR', $NO_2$, $NH_2$, NHR', or $NR'_2$, in which each R' is $C_1$–$C_6$-alkyl, $R^2$ is $C_1$–$C_4$-alkoxy, $R^3$ is hydrogen, fluorine, chlorine, or bromine, and $R^4$ and $R^5$, independently of one another, are hydrogen, fluorine, chlorine, bromine, $C_1$–$C_6$-alkyl, or $C_1$-$C_6$-alkoxy, comprising (1) in a first stage, selectively monometalating a bromine compound of the formula

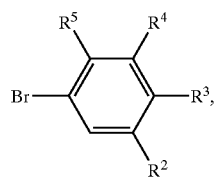

in which $R^2$ to $R^5$ have the meanings given for formula (I), in a solvent comprising a mixture of tetrahydrofuran and an aromatic hydrocarbon and reacting the resultant metalated compound with a diphenylphosphinic chloride of the formula (II)

in which $R^1$ has the meaning given for formula (I), which is added without solvent to the metalated compound, to give a diphenylphosphine oxide of the formula (III)

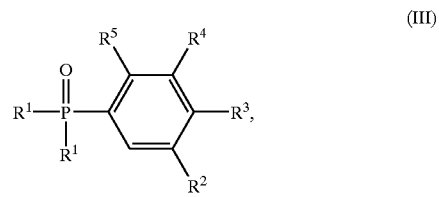

in which $R^1$ to $R^5$ have the meanings given in formula (I), which is isolated from a solution in an aromatic hydrocarbon by adding a saturated aliphatic hydrocarbon, (2) in a second stage, metalating the diphenylphosphine oxide of the formula (III) in the 6-position and reacting the resultant metalated compound with iodine at a temperature of not less than –25° C., wherein the metalated diphenylphosphine oxide of the formula (III) and iodine are metered in simultaneously such that a small amount of iodine is always present in excess, to give a 2-iodo-diphenyl-phosphine oxide of the formula (IV)

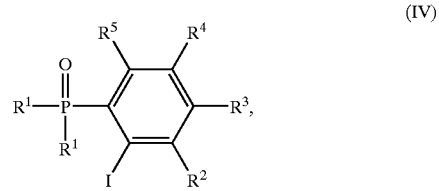

in which $R^1$ to $R^5$ have the meanings given for formula (I), which is separated off in dissolved form in an aromatic hydrocarbon, (3) in a third stage, converting the 2-iodo-diphenylphosphine oxide of the formula (IV) with copper in an aromatic hydrocarbon solvent into a racemic bis-diphenylphosphine oxide of the formula (I), which is crystallized from a solution in an aromatic hydrocarbon, and (4) in a fourth stage, separating the racemic bis-diphenylphosphine oxide of the formula (I) into its enantiomers by crystallization with an enantiomerically pure mono- or dicarboxylic acid, wherein a first enantiomer is obtained by crystallization from a solution in an aromatic hydrocarbon and a second enantiomer is obtained by hydrolysis and subsequent crystallization from a solution in an aromatic hydrocarbon.

2. A process according to claim 1 wherein $R^1$ is unsubstituted phenyl, unsubstituted naphthyl, heteroaryl having 4 or 5 carbon atoms and 1 or 2 heteroatoms selected from the group consisting of oxygen or sulfur, or unsubstituted cyclohexyl, $R^2$ is methoxy, $R^3$ is fluorine or chlorine, and $R^4$ and $R^5$ are hydrogen.

3. A process according to claim 1 wherein the aromatic hydrocarbon is benzene, toluene, or xylenes.

4. A process according to claim 1 wherein the saturated aliphatic hydrocarbon is a straight-chain or branched pentane, hexane, or octane.

5. A process according to claim 1 wherein in the first stage, 1 to 1.5 mol of magnesium, based on 1 mol of bromine compound of the formula (IIa), are used; the solvent is a mixture of 20 to virtually 100% by volume of tetrahydrofuran brought to 100% by volume using an aromatic hydrocarbon; and the precipitate formed after the addition of the saturated aliphatic hydrocarbon is filtered off 5 to 20 hours after the addition.

6. A process according to claim 1 wherein in the second stage, the diphenylphosphine oxide of the formula (III) is metalated at −25° C. to 0° C. in tetrahydrofuran, a solution of iodine in tetrahydrofuran is prepared separately, and the solutions of diphenylphosphine oxide and iodine are metered in to an initial charge of tetrahydrofuran at −25° C. to 0° C. such that a slight amount of iodine is always present in excess; excess iodine is removed; and 2-iodo-diphenylphosphine oxides of the formula (IV) are separated off in the form of 15 to 30% strength by weight of a solution in the aromatic hydrocarbon.

7. A process according to claim 1 wherein in the third stage, dendritic copper with an average particle size of from 1 to 100 μm, a surface area of from 0.04 to 1 m²/g, and a purity of more than 99.5% is initially introduced together with aromatic solvent and, at 70 to 140° C. the solution of 2-iodo-diphenylphosphine oxide of the formula (IV) obtained in the second stage is added in quantities such that 1 to 10 mol of dendritic copper is used per mole of 2-iodo-diphenylphosphine oxide of the formula (IV), with a metered addition and after-stirring period totaling 3 to 8 hours being used; and racemic bis-diphenylphosphine oxide of the formula (I) is crystallized by cooling to 0 to 25° C.

8. A process according to claim 1 wherein in the fourth stage, the racemic bis-diphenylphosphine oxide of the formula (I) is dissolved in a chlorinated hydrocarbon and reacted at elevated temperature with an enantiomerically pure dibenzoyltartaric acid, dissolved in an ester; and, by cooling a solution in an aromatic hydrocarbon to 0° C. to 30° C., a first enantiomerically pure form of the bis-diphenylphosphine oxide of the formula (I) is obtained.

9. A process according to claim 8 wherein a solution in an aromatic hydrocarbon is prepared from the filtrate from the work-up following the reaction with an enantiomerically pure dibenzoyltartaric acid, and concentrated by evaporation and cooling to obtain first a racemic feed material and then further concentrated by evaporation and cooling to obtain a second enantiomerically pure form of the bis-diphenylphosphine oxide of the formula (I).

* * * * *